(12) United States Patent
Fukushi et al.

(10) Patent No.: US 10,417,386 B2
(45) Date of Patent: Sep. 17, 2019

(54) INFORMATION PROCESSING DEVICE AND METHOD

(71) Applicant: Sony Corporation, Tokyo (JP)

(72) Inventors: Gakuho Fukushi, Tokyo (JP); Yoshinori Takagi, Kanagawa (JP); Shinsuke Araya, Kanagawa (JP); Yuya Horiuchi, Tokyo (JP)

(73) Assignee: Sony Corporation, Tokyo (JP)

( * ) Notice: Subject to any disclaimer, the term of this patent is extended or adjusted under 35 U.S.C. 154(b) by 1154 days.

(21) Appl. No.: 14/416,683

(22) PCT Filed: Jul. 18, 2013

(86) PCT No.: PCT/JP2013/069508
§ 371 (c)(1),
(2) Date: Apr. 15, 2015

(87) PCT Pub. No.: WO2014/021114
PCT Pub. Date: Feb. 6, 2014

(65) Prior Publication Data
US 2015/0227715 A1    Aug. 13, 2015

(30) Foreign Application Priority Data

Jul. 30, 2012 (JP) .............................. 2012-168033

(51) Int. Cl.
| G06F 19/00 | (2018.01) |
| G06Q 50/24 | (2012.01) |
| G06Q 10/10 | (2012.01) |

(52) U.S. Cl.
CPC ....... *G06F 19/3456* (2013.01); *G06Q 10/109* (2013.01); *G06Q 50/24* (2013.01)

(58) Field of Classification Search
USPC ....................................................... 705/2–4
(Continued)

(56) References Cited

U.S. PATENT DOCUMENTS

| 7,996,243 B1* | 8/2011 | Ali ........................ G06Q 50/22 |
|  |  | 705/2 |
| 8,930,203 B2* | 1/2015 | Kiaie ................. A61B 5/14532 |
|  |  | 705/2 |

(Continued)

FOREIGN PATENT DOCUMENTS

| JP | 2004-029985 | 1/2004 |
| JP | 2006-155071 | 6/2006 |

(Continued)

OTHER PUBLICATIONS

Grimes, Tamasine C., et al. "Medication details documented on hospital discharge: cross-sectional observational study of factors associated with medication non-reconciliation." British journal of clinical pharmacology 71.3 (2011): 449-457.*

(Continued)

*Primary Examiner* — Mark Holcomb
(74) *Attorney, Agent, or Firm* — Chip Law Group

(57) ABSTRACT

There is provided an information processing device including an acquisition unit configured to acquire a date of prescription of a prescription drug and the number of days of prescription of the prescription drug, a calculation unit to carry out division based on the number of days of prescription of the prescription drug and the number of days of prescription of another prescription drug and identify whether or not the prescription drug is a long-acting medicine based on whether or not a result of the division satisfies a predetermined condition, and a medication schedule generation unit to generate medication schedule information of the prescription drug based on the date of prescription of the prescription drug and the number of days of prescription of the other prescription drug when the prescription drug is the long-acting medicine.

7 Claims, 10 Drawing Sheets

(58) Field of Classification Search
IPC .................................................. G06F 19/3456
See application file for complete search history.

(56) References Cited

U.S. PATENT DOCUMENTS

| | | | | |
|---|---|---|---|---|
| 2002/0116222 | A1* | 8/2002 | Wurster | G06Q 10/10 |
| | | | | 705/2 |
| 2002/0165736 | A1* | 11/2002 | Tolle | G06F 19/328 |
| | | | | 705/3 |
| 2003/0236681 | A1 | 12/2003 | Ninomiya et al. | |
| 2006/0253299 | A1 | 11/2006 | Konishi et al. | |
| 2009/0198517 | A1* | 8/2009 | Ruben | G06Q 10/087 |
| | | | | 705/3 |
| 2011/0000170 | A1* | 1/2011 | Burg | G06F 19/3462 |
| | | | | 53/474 |
| 2011/0196696 | A1* | 8/2011 | Akers | G06F 19/328 |
| | | | | 705/2 |
| 2012/0126958 | A1 | 5/2012 | Kim et al. | |

FOREIGN PATENT DOCUMENTS

| | | |
|---|---|---|
| JP | 2006-155071 A | 6/2006 |
| JP | 2007-501983 | 2/2007 |
| JP | 2009-245255 A | 10/2009 |

OTHER PUBLICATIONS

International Search Report issued in connection with International Patent Application No. PCT/JP2013/069508, dated Oct. 22, 2013. (1 page).

Office Action for JP Patent Application No. 2018-117634, dated Jun. 20, 2019, 3 pages Of Office Action and 2 pages Of English Translation.

* cited by examiner

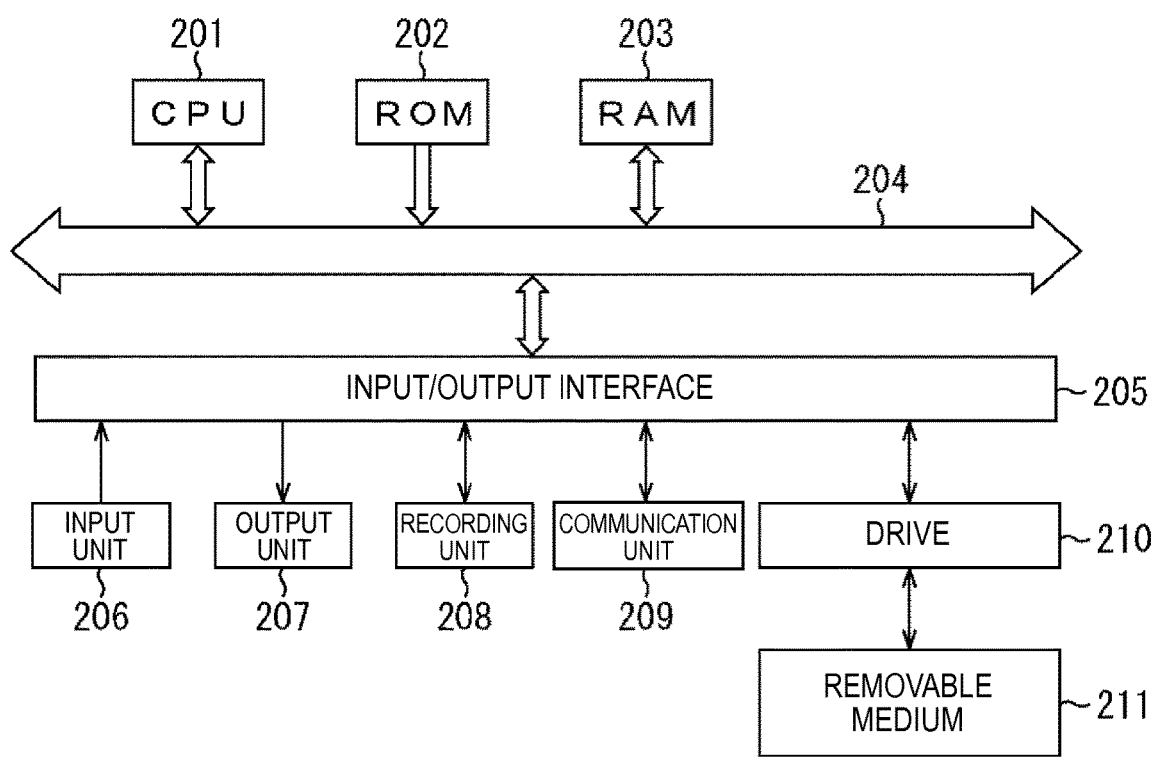

INFORMATION PROCESSING DEVICE AND METHOD

CROSS REFERENCES TO RELATED APPLICATIONS

The present application is a national stage of International Application No. PCT/JP2013/069508 filed on Jul. 18, 2013 and claims priority to Japanese Patent Application No. 2012-168033 filed on Jul. 30, 2012, the disclosure of which is incorporated herein by reference.

BACKGROUND

The present invention relates to an information processing device, a method, and a program, and particularly relates to an information processing device, a method, and a program that are capable of obtaining more probable information on medication.

While print media are employed for prescriptions issued by doctors and Medication Notebooks issued in pharmacies, there is a demand for construction of a mechanism to electronically share and manage prescriptions and Medication Notebooks from the perspective of improvement in convenience and efficiency.

With that, a technique is proposed that achieves safe prescription of drugs by managing prescription information of each patient in a medicine prescription apparatus (see, for example, Patent Literature 1). In this technique, when a user, who is a patient, accesses a medicine prescription apparatus, the medicine prescription apparatus selects prescription information that satisfies prescription conditions determined by a doctor from prescription information of the patient and sends the selected information to a portable terminal of the patient.

Then, when the patient specifies a desired one from the prescription information displayed on the portable terminal, the prescription information is published to a dispensary by the medicine prescription apparatus. After that, when the patient visits the dispensary and personal authentication and the like are performed, the drug is dispensed by a pharmacist at the dispensary based on the prescription information and handed over to the patient.

CITATION LIST

Patent Literature

Patent Literature 1: JP 2004-029985A

SUMMARY

Technical Problem

In the case where prescriptions and health insurance claims are electronized, it is possible to extract a date of prescription and the number of days of prescription of each prescription drug that is prescribed for a patient from medication history information, such as health insurance claims, so that it is also possible to figure out a medication schedule of each prescription drug. Using the medication schedule thus obtained, it is enabled to prevent duplication of drugs and prescription of a drug to be contraindication to intake combination to a user, who is a patient.

For example, in the case where Dj and Mj are extracted from an electronized health insurance claim or the like as a date of prescription and the number of days of prescription of a prescription drug, the prescription drug is taken by a patient in a period from a date of prescription Dj to Dj+Mj−1. In this case, it is assumed that the patient takes the prescription drug every day from the date of prescription, and detection of a drug to be contraindication to intake combination and the like are performed on the assumption that the prescription drug is taken by the patient in the period from Dj to Dj+Mj−1.

However, as an antirheumatic medicine Rheumatrex®, there are also drugs having an effect of an intake acting for one week. For example, when Rheumatrex is prescribed for two weeks, the number of days of prescription that is obtained from the medication history information, such as health insurance claims, turns out to be for two days. This is because the health insurance claims are not medication calendars but are bills for drugs, so that recording is made in the form of prescription for two days.

For example, a case is considered where the date of prescription of Rheumatrex that is obtained from the health insurance claims is Dj. In this case, the dates when the patient actually takes the drug are the day Dj and the day (Dj+7) while the number of days of prescription that is obtained from the health insurance claims is two days, so that the process turns out to be performed as Rheumatrex is taken on the day Dj and the day (Dj+1) and a gap occurs in the medication schedule.

It should be noted that, in the descriptions below, a drug having an effect of drug medication acting for several days is referred to as a long-acting medicine. There are also many of such long-acting medicines other than Rheumatrex.

For example, among Fosamac® tablets and Bonalon® tablets as medicines for osteoporosis, there are a type to be taken once a day and a type to be taken once a week.

Specifically, Fosamac tablets 5 mg and Bonalon tablets 5 mg are taken once (one tablet) a day, and Fosamac tablets 35 mg and Bonalon tablets 35 mg are taken once (one tablet) a week and the effects act for seven days.

In the present circumstances, medication schedules of such long-acting medicines are handled by adding a special report or the like in individual health insurance claims. In medical settings and conventional computers for health insurance claims where accuracy of processing is required more than temporal processing speed, information on medication of long-acting medicines may be inputted as a special report. However, in collective processing, such as analysis of health insurance claims, it is not realistic to perform separate processing for each prescription drug from the perspective of an increase in calculation amount. Moreover, the special report is often lost from collective processing for analysis of health insurance claims.

As described above, in the technique described above, regarding a prescription drug that is prescribed for a patient, it has been difficult to obtain accurate information on medication of the prescription drug.

The present disclosure has been made in view of such circumstances and is capable of obtaining more probable information on medication.

Solution to Problem

According to an aspect of the present technology, there is provided an information processing device including an acquisition unit configured to acquire a date of prescription of a prescription drug and the number of days of prescription of the prescription drug, a calculation unit configured to carry out division based on the number of days of prescription of the prescription drug and the number of days of prescription of another prescription drug and identify whether or not the prescription drug is a long-acting medicine based on whether or not a result of the division satisfies a predetermined condition, and a medication schedule generation unit configured to generate medication schedule information of the prescription drug based on the date of prescription of the prescription drug and the number of days of prescription of the other prescription drug when the prescription drug is the long-acting medicine.

The calculation unit may carry out division based on the number of days of prescription of the prescription drug and the number of days of prescription of the other prescription drug having a date of prescription same as the prescription drug.

The medication schedule generation unit may generate the medication schedule information on an assumption that the number of days of prescription of the prescription drug is same as the number of days of prescription of the other prescription drug.

The medication schedule generation unit may divide a period of the number of days of prescription of the other prescription drug having the date of prescription of the prescription drug as a starting date into the number of divided periods same as the number of days of prescription of the prescription drug that is acquired by the acquisition unit, and may generate the medication schedule information that indicates a medication schedule and a degree of influence of the prescription drug in a manner that the degree of influence due to the prescription drug attenuates from a starting date to a finishing date of the divided period in each of the divided periods.

The calculation unit may assume that the prescription drug is the long-acting medicine when a reminder of Ma/Mb is 0 in a case where the number of days of prescription of the other prescription drug is Ma, the number of days of prescription of the prescription drug is Mb, and Ma>Mb.

The calculation unit may assume that the prescription drug is the long-acting medicine when a quotient of Ma/(Mb−1) is any one of 7, 14, or 28 to 31 in a case where the number of days of prescription of the other prescription drug is Ma, the number of days of prescription of the prescription drug is Mb, and Ma>Mb.

The information processing device may further includes an identification unit configured to identify whether or not there is the other prescription drug having a date of prescription identical to the prescription drug and also having the number of days of prescription different from the prescription drug.

According to an aspect of the present technology, there is provided an information processing method including a step of acquiring a date of prescription of a prescription drug and the number of days of prescription of the prescription drug, a step of carrying out division based on the number of days of prescription of the prescription drug and the number of days of prescription of another prescription drug and identifying whether or not the prescription drug is a long-acting medicine based on whether or not a result of the division satisfies a predetermined condition, and a step of generating medication schedule information of the prescription drug based on the date of prescription of the prescription drug and the number of days of prescription of the other prescription drug in a case where the prescription drug is the long-acting medicine.

According to an aspect of the present technology, acquiring a date of prescription of a prescription drug and the number of days of prescription of the prescription drug is performed, carrying out division based on the number of days of prescription of the prescription drug and the number of days of prescription of another prescription drug and identifying whether or not the prescription drug is a long-acting medicine based on whether or not a result of the division satisfies a predetermined condition are performed, and generating medication schedule information of the prescription drug based on the date of prescription of the prescription drug and the number of days of prescription of the other prescription drug in a case where the prescription drug is the long-acting medicine is performed.

Advantageous Effects of Invention

According to an embodiment of the present invention, it is possible to obtain more probable information on medication.

Additional features and advantages are described herein, and will be apparent from the following Detailed Description and the figures.

BRIEF DESCRIPTION OF THE FIGURES

FIG. 10 is an illustration of a configuration example of a computer.

DETAILED DESCRIPTION

Descriptions are given below to embodiments to which the present invention is applied with reference to the drawings.

First Embodiment

[Configuration Example of Information Processing System]

The present disclosure is to make possible to obtain more probable information on intake of a prescription drug when it is intended to execute processing, such as detection of duplication of drugs and contraindication to intake combination of drugs, utilizing, for example, a date of prescription and the number of days of prescription of a drug that is prescribed for a patient.

In the present circumstances, easily accessible information as information on prescription drugs, that is, medication history information is not a medication calendar indicating a medication schedule of a patient but invoice data, such as health insurance claims for medical treatment and health insurance claims for dispensation. Although these health insurance claims for medical treatment and health insurance claims for dispensation include a date of prescription and the number of days of prescription of a prescription drug, the number of days of prescription here is the number of days for the prescribed amount.

However, as described above, among drugs, there are drugs having an effect of taking the drugs acting (remaining) for a period longer than one day. Therefore, there is a case where the number of days of prescription extracted from health insurance claims for medical treatment or the like disagrees with the period for a patient to actually take the drug, that is, the number of days of the period during which the prescription drug keeps an effect of taking the drug.

With that, in the present disclosure, utilizing the respective numbers of days of prescription of a plurality of prescription drugs of an identical date of prescription, it becomes possible to obtain more probable information on medication of each prescription drug, that is, more probable information that indicates the number of days in a period for a patient to actually take the drugs (number of days of prescription).

In other words, in the present disclosure, by being associated with data of other drugs of an identical date of prescription, the lost information on the number of days of prescription of each prescription drug is complemented and thus it is enabled to obtain more probable information on medication of a prescription drug. For example, in the present disclosure, as the information on medication, medication schedule information indicating a medication schedule of each prescription drug of a user is generated.

Next, specific embodiments to which the present disclosure is applied are described.

Figure 1:
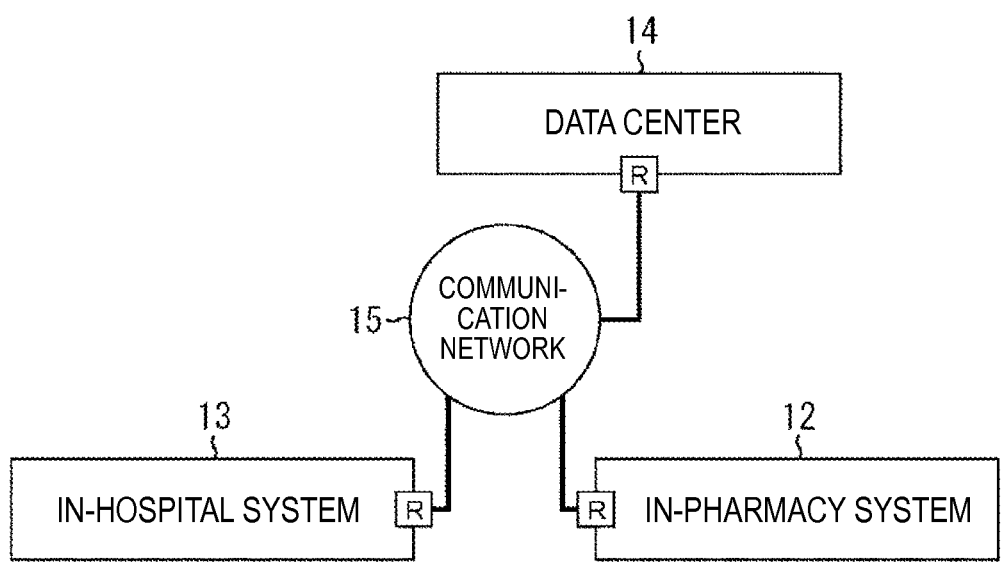
FIG. 1 is an illustration of a configuration example of an information processing system.
Figure 1:
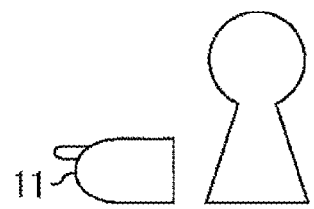

FIG. 1 is an illustration of a configuration example of one embodiment of an information processing system to which the present disclosure is applied.

The information processing system in FIG. 1 is configured with a portable terminal device 11, an in-pharmacy system 12, an in-hospital system 13, and a data center 14. The in-pharmacy system 12, the in-hospital system 13, and the data center 14 are connected to each other via a communication network 15 composed of wired and wireless networks, such as the Internet.

The portable terminal device 11 is composed of a mobile phone or the like belonging to a user and communicates with the in-pharmacy system 12, the in-hospital system 13, and data center 14 via the communication network 15 or a communication network (not shown) to exchange information as needed.

The in-pharmacy system 12 is installed in a pharmacy where a user purchases a prescribed drug and is configured with one or a plurality of devices. The in-pharmacy system 12 communicates with the portable terminal device 11 to exchange necessary information with the portable terminal device 11 and performs various processes in response to an input operation by a pharmacist or the like.

In addition, in the in-pharmacy system 12, private/medication history information that is composed of private information of a user, who is a patient, data on a medication history (hereinafter, referred to as medication history data), a dispensary ID to identify the in-pharmacy system 12, and the like, dispensation health insurance claim information, and the like are recorded for each user.

The medication history data of each user includes information on drugs dispensed for the user in a pharmacy or the like, information on prescriptions of the drugs, a medication history ID to identify the medication history data, or the like. More specifically, for example, the medication history data includes information, such as information indicating prescribed drugs, a date of prescription and the number of days of prescription of the drugs, and medication history ID.

In addition, the dispensation health insurance claim information is electronized health insurance claims, and the dispensation health insurance claim information includes information, such as names of drugs prescribed for the user, a date of prescription, the number of days of prescription, and a health insurance claim ID to identify the dispensation health insurance claim information.

The in-pharmacy system 12 generates the private/medication history information and the dispensation health insurance claim information as needed for recording and sends the medication history data included in the private/medication history information, the dispensation health insurance claim information, and the like to the data center 14.

The in-hospital system 13 is installed in a hospital where a user, who is a patient, attends and is configured with one or a plurality of devices. The in-hospital system 13 communicates with the portable terminal device 11 to exchange necessary information with the portable terminal device 11 and performs various processes in response to an input operation by a doctor or the like.

In addition, in the in-hospital system 13, private/consultation information that is composed of private information of a user, who is a patient, data on consultation (hereinafter, referred to as consultation data), a medical institution ID to identify the in-hospital system 13, and the like, medical health insurance claim information, diagnosis procedure combination (DPC) health insurance claim information and the like are recorded for each user. For example, the consultation data is supposed to be an electronic health record or the like.

It should be noted that, for example, the medical health insurance claim information and the DPC health insurance claim information include information, such as a drug name of a drug prescribed for a user, who is a patient, a date of prescription and the number of days of prescription of the drug, and a health insurance claim ID to identify the medical health insurance claim information and the health insurance claim information for the prescription.

The in-hospital system 13 generates the private/consultation information, the medical health insurance claim information, and the DPC health insurance claim information as needed for recording and sends the consultation data included in the private/consultation information, the medical health insurance claim information, and the DPC health insurance claim information to the data center 14.

The data center 14 is configured with one or a plurality of devices. The data center 14 receives the medication history data, the consultation data, the dispensation health insurance claim information, the medical health insurance claim information, the DPC health insurance claim information, and the like from the in-pharmacy system 12 and the in-hospital system 13 for recording and sends such data to the in-pharmacy system 12, the in-hospital system 13, and the portable terminal device 11 as requested. That is to say, the respective information such as the medication history data and the consultation data that is recorded in the data center 14 is shared respectively by the in-pharmacy system 12, the in-hospital system 13, and the portable terminal device 11.

When receiving the medication history data or the consultation data, the data center 14 updates user medication history information. The user medication history information includes a personal identification ID of a user, the dispensary ID or the medical institution ID, the medication history data or the consultation data, contact information, such as an electronic mail address, of the user, and the like.

[Configuration Example of Data Center]

Figure 2:
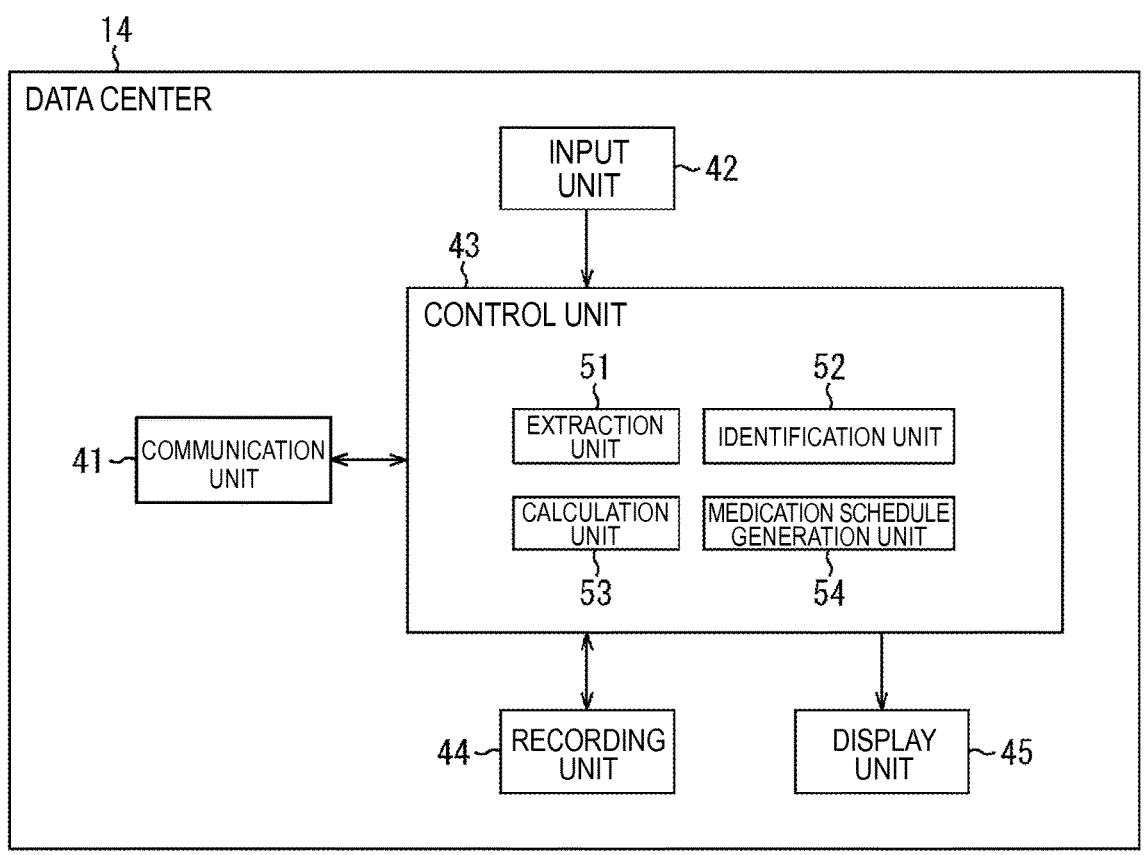
FIG. 2 is an illustration of a configuration example of a data center.

Subsequently, descriptions are given to a more detailed configuration of the data center 14 in FIG. 1. FIG. 2 is an illustration of a more detailed configuration example of the data center 14.

The data center 14 is configured with a communication unit 41, an input unit 42, a control unit 43, a recording unit 44, and a display unit 45.

The communication unit 41 communicates with an external device, such as the portable terminal device 11, receives various types of data to supply the data to the control unit 43, and sends the data supplied from the control unit 43. The input unit 42 is composed of, for example, input buttons, a touch screen, and the like and supplies the information inputted by an administrator of the data center 14 to the control unit 43.

The control unit 43 controls behaviors of the entire data center 14. The control unit 43 is provided with an extraction unit 51, an identification unit 52, a calculation unit 53, and a medication schedule generation unit 54.

The extraction unit 51 extracts information on a prescription drug that is prescribed for a patient, such as a drug name, a date of prescription, and the number of days of prescription of the prescription drug, for example from the medication history information, such as the medical health insurance claim information, recorded in the recording unit 44. The identification unit 52 identifies prescription drugs of an identical date of prescription based on the date of prescription of each of the extracted prescription drugs.

The calculation unit 53 performs division based on the numbers of days of prescription of the prescription drugs of an identical date of prescription and determines whether or not the result of the division satisfies a predetermined condition to identify that the prescription drugs are long-acting medicines. The medication schedule generation unit 54 generates medication schedule information for each prescription drug based on the result of identifying long-acting medicines.

The recording unit 44 records programs executed by the control unit 43 and various types of data and supplies such data to the control unit 43. For example, the recording unit 44 records the user medication history information, the dispensation health insurance claim information, the medical health insurance claim information, the DPC health insurance claim information, and the like. The display unit 45 is composed of a liquid crystal display panel or the like and displays various images based on the data supplied from the control unit 43.

[Description of Medication Schedule Generation Process]

When, for example, a user operates the portable terminal device 11 to launch an application program for notification of a risk of combination of intake drugs, the portable terminal device 11 requests sending of medication schedule information of prescription drugs for a specific patient to the data center 14.

The data center 14 then performs medication schedule generation process in response to the request from the portable terminal device 11 to generate the medication schedule information and sends the generated information to the portable terminal device 11.

Descriptions are given below to medication schedule generation process by the data center 14 with reference to a flow chart in FIG. 3. It should be noted that the medication schedule generation process is executed for each health insurance claim, such as medical health insurance claim information that is identified by a health insurance claim ID, for example.

In step S11, the extraction unit 51 extracts a date of prescription and the number of days of prescription of each prescription drug as information on a prescription drug that is prescribed for a specific patient from the medication history information, such as the dispensation health insurance claim information, the medical health insurance claim information, and the DPC health insurance claim information, recorded in the recording unit 44. That is to say, the extraction unit 51 acquires a date of prescription and the number of days of prescription of prescription drugs from the recording unit 44.

In step S12, the identification unit 52 determines whether or not there are drugs having different numbers of days of prescription on an identical date of prescription.

For example, it is assumed that, where a date of prescription and the number of days of prescription of a prescription drug A in prescription a are Da and Ma, respectively, and a date of prescription and the number of days of prescription of a prescription drug B in prescription b are Db and Mb, respectively, information on the prescription drug A and the prescription drug B is extracted from the medical health insurance claim information.

In this case, for the prescription drug A and the prescription drug B subjected to the process, the identification unit 52 compares the date of prescription Da with the date of prescription Db and the number of days of prescription Ma with the number of days of prescription Mb, respectively. Then, in the case of the date of prescription Da=Db and also the number of days of prescription Ma≠Mb, that is, in the case where the prescription drug A and the prescription drug B have a same date of prescription while having different numbers of days of prescription, the identification unit 52 determines that there are drugs having different numbers of days of prescription on an identical date of prescription.

Usually, when a plurality of drugs is prescribed on a same day, there is a high possibility that these drugs have a same number of days of prescription. With that, the data center 14 performs subsequent processes on the assumption that prescription drugs having a same date of prescription and also a same number of days of prescription are not long-acting medicines. On the contrary, when there are prescription drugs having different numbers of days of prescription while the date of prescription is same, there is a high possibility that at least one of such prescription drugs is a long-acting medicine, so that determination process on whether or not each prescription drug is a long-acting medicine is performed.

When determined that there is a drug having a different number of days of prescription on an identical date of prescription in step S12, the identification unit 52 determines whether or not the prescription drug subjected to the process is an as-needed medicine in step S13. Here, an as-needed medicine is a drug that is taken only when a symptom develops.

For example, when the prescription drug subjected to the process is extracted from the dispensation health insurance claim information that is recorded in the recording unit 44, the identification unit 52 determines whether or not the prescription drug is an as-needed medicine by referring to a dosage form code included in the dispensation health insurance claim information. A dosage form code indicates which one of internal use, drops for internal use, as-needed, injection, and the like a prescription drug is, and when the dosage form indicates "as-needed", the identification unit 52 determines that the prescription drug is an as-needed medicine.

In addition for example, when the prescription drug subjected to the process is extracted from the medical health insurance claim information that is recorded in the recording unit 44, the identification unit 52 determines whether or not the prescription drug is an as-needed medicine by referring to a medical practice identification code included in the medical health insurance claim information. A medical practice identification code includes a code indicating which one of internal use, as-needed, external use, and the like the administrated drug is, and when the medical practice identification code indicates "as-needed", the identification unit 52 determines that the prescription drug is an as-needed medicine.

As just described, the dispensation health insurance claim information and the medical health insurance claim information that are used generally include information, such as the dosage form code and the medical practice identification code, that allows identification of whether or not the prescription drug is an as-needed medicine, so that the identification unit 52 determines whether or not the prescription drug is an as-needed medicine referring to such information.

When determined that the prescription drug is not an as-needed medicine in step S13, the calculation unit 53 carries out division based on the extracted number of days of prescription of the prescription drug in step S14.

For example, it is assumed that the number of days of prescription of the prescription drug A is Ma, the number of days of prescription of the prescription drug B is Mb, and Ma>Mb.

In this case, the calculation unit 53 obtains a reminder Z when dividing the number of days of prescription Ma by the number of days of prescription Mb. Then, when the reminder Z of Ma/Mb is 0, the calculation unit 53 assumes that the prescription drug B is a long-acting medicine.

For example, medicines to be gradually accumulated in the body, such as Rheumatrex, and medicines for osteoporosis, such as Bonalon tablets, are long-acting medicines that are taken in such a method as to be taken once to three times a week.

Now, it is assumed that, for example, the prescription drug A is a drug to be taken every day and the prescription drug B is a long-acting medicine to be taken once a week, and the prescription drug A and the prescription drug B are prescribed in an amount for two weeks. At this time, the prescription drug A is taken every day and Ma=14 and the prescription drug B is taken only once a week and Mb=2, so that the reminder Z of Ma/Mb=14/2 becomes 0.

As just described, when the reminder Z is 0, the prescription drug B may be assumed as a long-acting medicine.

In addition, for example, the calculation unit 53 obtains a quotient Q when dividing the number of days of prescription Ma by a value (Mb−1) obtained by subtracting 1 from the number of days of prescription Mb. Then, the calculation unit 53 assumes that the prescription drug B is a long-acting medicine when the quotient Q of Ma/(Mb−1) is any one of 7, 14, or 28 to 31.

For example, it is assumed that, for example, the prescription drug A is a drug to be taken every day and the prescription drug B is a long-acting medicine to be taken twice a week, and the prescription drug A and the prescription drug B are prescribed in an amount for one week. At this time, the prescription drug A is taken every day and Ma=7 and the prescription drug B is taken twice a week and Mb=2, so that the quotient Q of Ma/(Mb−1)=7/(2−1) becomes 7.

In addition, it is assumed that, for example, the prescription drug A is a drug to be taken every day and the prescription drug B is a long-acting medicine to be taken once a week, and the prescription drug A and the prescription drug B are prescribed in an amount for two weeks. At this time, the prescription drug A is taken every day and Ma=14 and the prescription drug B is taken once a week and Mb=2, so that the quotient Q of Ma/(Mb−1)=14/(2−1) becomes 14.

Further, it is assumed that, for example, the prescription drug A is a drug to be taken every day and the prescription drug B is a long-acting medicine to be taken once in two weeks, and the prescription drug A and the prescription drug B are prescribed in an amount for one month. At this time, the prescription drug A is taken every day and Ma=any one from 28 to 31 and the prescription drug B is taken once in two weeks and Mb=2, so that the quotient Q of Ma/(Mb−1) becomes any one from 28 to 31.

As just described, when the quotient Q of Ma/(Mb−1) is any one from 28 to 31, the prescription drug B may be assumed as a long-acting medicine. In this case, even when the reminder of Ma/(Mb−1) does not become 0 due to the number of days of prescription of the prescription drug A or the like, it is possible to identify whether or not the prescription drug B is a long-acting medicine.

In step S15, the calculation unit 53 determines whether or not the prescription drug is a long-acting medicine based on the result of the division on the basis of the extracted number of days of prescription of the prescription drug.

For example, regarding the prescription drug A and the prescription drug B where Ma>Mb, when the reminder Z of Ma/Mb is 0 or when the quotient Q of Ma/(Mb−1) is any one of 7, 14, or from 28 to 31, the calculation unit 53 determines that the prescription drug B is a long-acting medicine.

When determined as a long-acting medicine in step S15, the medication schedule generation unit 54 performs long-acting medicine process to generate medication schedule information in step S16.

For example, when the prescription drug B is determined as a long-acting medicine among the prescription drug A, having the date of prescription Da and the number of days of prescription Ma, and the prescription drug B, having the date of prescription Db and the number of days of prescription Mb, the medication schedule generation unit 54 generates medication schedule information making the number of days of prescription Mb of the prescription drug B as Ma. It should be noted that Ma>Mb.

Figure 4:
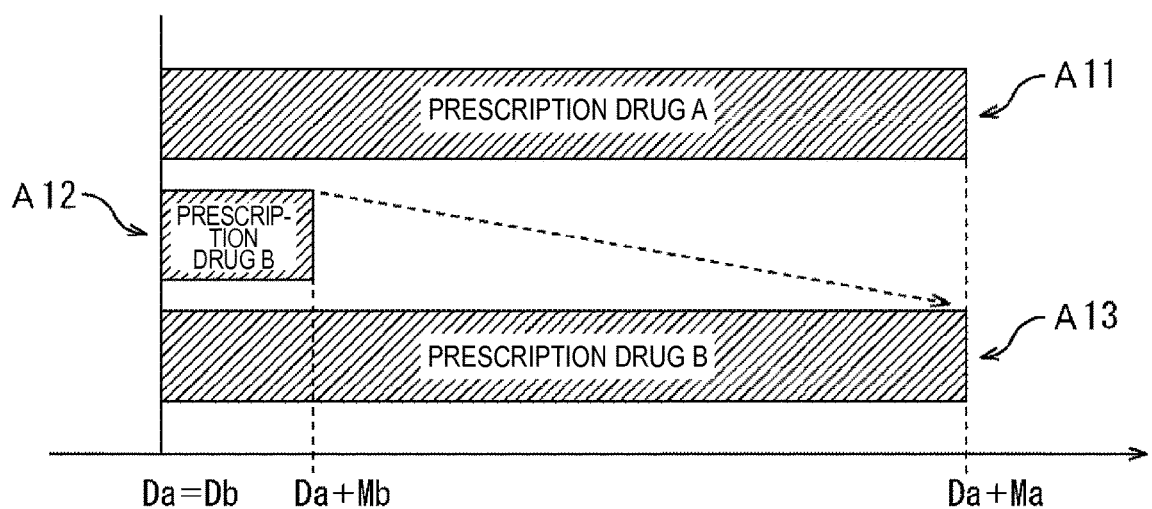
FIG. 4 is an illustration of one example of medication schedule information.

Thus, the medication schedule information illustrated in FIG. 4, for example, is obtained. It should be noted that the horizontal direction in FIG. 4 indicates dates.

In the example of FIG. 4, a rectangle indicated by an arrow A11 illustrates the medication schedule information of the prescription drug A. In addition, a rectangle indicated by an arrow A12 illustrates the medication schedule information when the prescription drug B is not a long-acting medicine, and a rectangle indicated by an arrow A13 illustrates the medication schedule information when the prescription drug B is a long-acting medicine.

In the medication schedule information of the prescription drug A indicated by the arrow A11, left end and right end positions of the rectangle representing the medication schedule information in FIG. 4 indicate a date of starting medication and a date of finishing medication of the prescription drug A, respectively. Specifically, the date of starting medication of the prescription drug A is a date of prescription Da, and the date of finishing medication of the prescription drug A is (Da+Ma−1).

Therefore, according to the medication schedule information of the prescription drug A indicated by the arrow A11, it is understood that a user is medicated with the prescription drug A in a period from the date of prescription Da to (Da+Ma−1), that is, for Ma days as the number of days of prescription.

In addition, in the case where medication schedule information is generated from the date of prescription Db and the number of days of prescription Mb of the prescription drug B, the medication schedule information indicated by the arrow A12 is obtained.

In the medication schedule information of the prescription drug B indicated by the arrow A12, left end and right end positions of the rectangle representing the medication schedule information in FIG. 4 indicate a date of starting medication and a date of finishing medication of the prescription drug B, respectively. Specifically, the date of starting medication of the prescription drug B is the date of prescription Da=Db, and the date of finishing medication of the prescription drug B is (Da+Mb−1).

In the medication schedule information indicated by the arrow A12, it is unnatural that, although the prescription drug A and the prescription drug B are prescribed on a same day, the period of medication of the prescription drug B is significantly shorter than the period of medication of the prescription drug A. As just described, when the prescription drug B is a long-acting medicine, a correct medication schedule is not obtained by generating medication schedule information from the date of prescription Db and the number of days of prescription Mb of the prescription drug B in a process similar to other drugs that are not long-acting medicines.

With that, the medication schedule generation unit 54 generates medication schedule information on the assumption that the number of days of prescription Mb of the prescription drug B is Mb=Ma. That is, the medication schedule information is generated on the assumption that the number of days of prescription of the prescription drug B is not Mb but Ma actually. Thus, the medication schedule information of the prescription drug B indicated by the arrow A13 is obtained.

In the medication schedule information of the prescription drug B indicated by the arrow A13, left end and right end positions of the rectangle representing the medication schedule information in FIG. 4 indicate a date of starting medication and a date of finishing medication of the prescription drug B, respectively. Specifically, the date of starting medication of the prescription drug B is the date of prescription Da=Db, and the date of finishing medication of the prescription drug B is (Da+Ma−1). That is, the period of medication of the prescription drug B is same as the period of medication of the prescription drug A.

In such a manner, it is possible to obtain medication schedule information that indicates a more probable medication schedule by appropriately correcting the number of days of prescription Mb of the prescription drug B based on the number of days of prescription Ma of the prescription drug A prescribed on a same day. It should be noted that, hereinafter, the process of changing a medication schedule of a long-acting medicine utilizing the number of days of prescription of a prescription drug that is prescribed on a same day as the long-acting medicine may also be referred to as long-acting medicine process.

In addition, for example, the number of days of prescription of the prescription drug B that is considered as a long-acting medicine may also be handled as a periodic fading coefficient of Mb times. That is to say, a periodic influence distribution of the effect of the drug over Mb times may be outputted as the medication schedule information of the prescription drug B.

Figure 5:
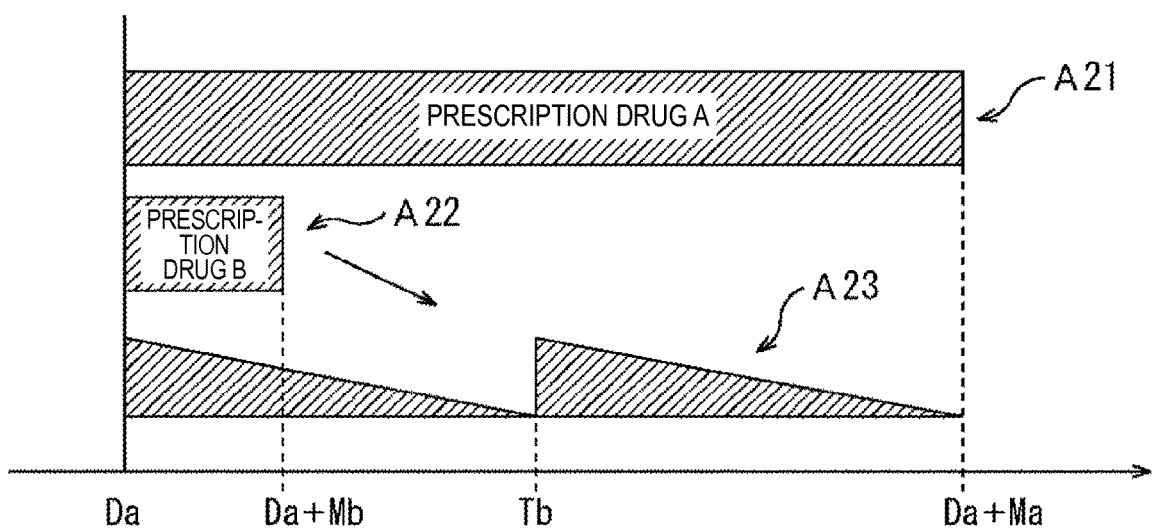
FIG. 5 is an illustration of one example of medication schedule information.

In such a case, for example, the medication schedule generation unit 54 generates the medication schedule information illustrated in FIG. 5. It should be noted that the horizontal direction in FIG. 4 indicates dates. In addition, FIG. 5 illustrates an example in the case of the number of days of prescription Mb=2.

In the example of FIG. 5, the rectangle indicated by an arrow A21 illustrates the medication schedule information of the prescription drug A. In addition, the rectangle illustrated by an arrow A22 illustrates the medication schedule information when the prescription drug B is not a long-acting medicine, and a plurality of triangles indicated by an arrow A23 illustrate the medication schedule information when the prescription drug B is a long-acting medicine.

The medication schedule information of the prescription drug A indicated by the arrow A21 and the medication schedule information of the prescription drug B indicated by the arrow A22 are similar to the medication schedule information indicated by the arrow A11 in FIG. 4 and the medication schedule information indicated by the arrow A12, so that their descriptions are omitted.

In addition, in the medication schedule information of the prescription drug B indicated by the arrow A23, the vertical direction in FIG. 5 indicates a degree of influence of the prescription drug B due to medication to a user, and left end and right end positions of the graphics representing the medication schedule information in FIG. 5 indicate a date of starting medication and a date of finishing medication of the prescription drug B.

Upon generation of the medication schedule information of the prescription drug B indicated by the arrow A23, the medication schedule generation unit 54 firstly makes the period of medication of the prescription drug B as a period from the date of prescription Da=Db to Da+Ma−1 and also divides the period of medication into Mb periods (hereinafter, may also be referred to as divided periods).

Since Mb=2 in this example, the period of medication of the prescription drug B is divided into a period from the date of prescription Da to Tb and a period from Tb+1 to Da+Ma−1. Here, when an integer part of Ma/Mb is represented by [Ma/Mb], Tb becomes Da+[Ma/Mb].

Next, the medication schedule generation unit 54 makes the degree of influence on a starting date of each divided period to be a predetermined value, such as "1", for example. Further, the medication schedule generation unit 54 defines the degree of influence at each date in the divided period in such a manner that the degree of influence linearly fades (attenuates) until the finishing date of the divided period and the information indicating the degree of influence at each date is the medication schedule information indicated by the arrow A23.

In this example, in the period from Da to Tb and the period from Tb+1 to Da+Ma−1 that are the divided periods, the degree of influence of the prescription drug B, that is, the height of the graphic indicated by the arrow A23 in the vertical direction becomes linearly lower from the starting date to the finishing date of each divided period. Accordingly, the medication schedule information of the prescription drug B indicated by the arrow A23 becomes information in the form of two triangles in alignment.

This is because a user is assumed to take the prescription drug B on the starting date of each divided period. Specifically, in this example, the user takes the prescription drug B in Mb times in the period of medication of the prescription drug B, that is, in the period from the date of prescription Da to Da+Ma−1.

Firstly, the user takes the prescription drug B on the date of prescription Da. Accordingly, the degree of influence of the prescription drug B is high on the date of prescription Da, and after that, the degree of influence gradually becomes lower. Then, the user takes the prescription drug B on the day of date Tb+1. With that, the degree of influence on Tb+1 becomes high in response to the medication of the prescription drug B, and after that, the degree of influence gradually becomes lower until the finishing date of the period of medication.

As just described, it becomes possible to detect a risk of combination of intake drugs, duplication, and the like considering the temporal distance of each drug by generating the medication schedule information that indicates not only the schedule of medication but also the degree of influence of drugs due to medication.

Figure 3:
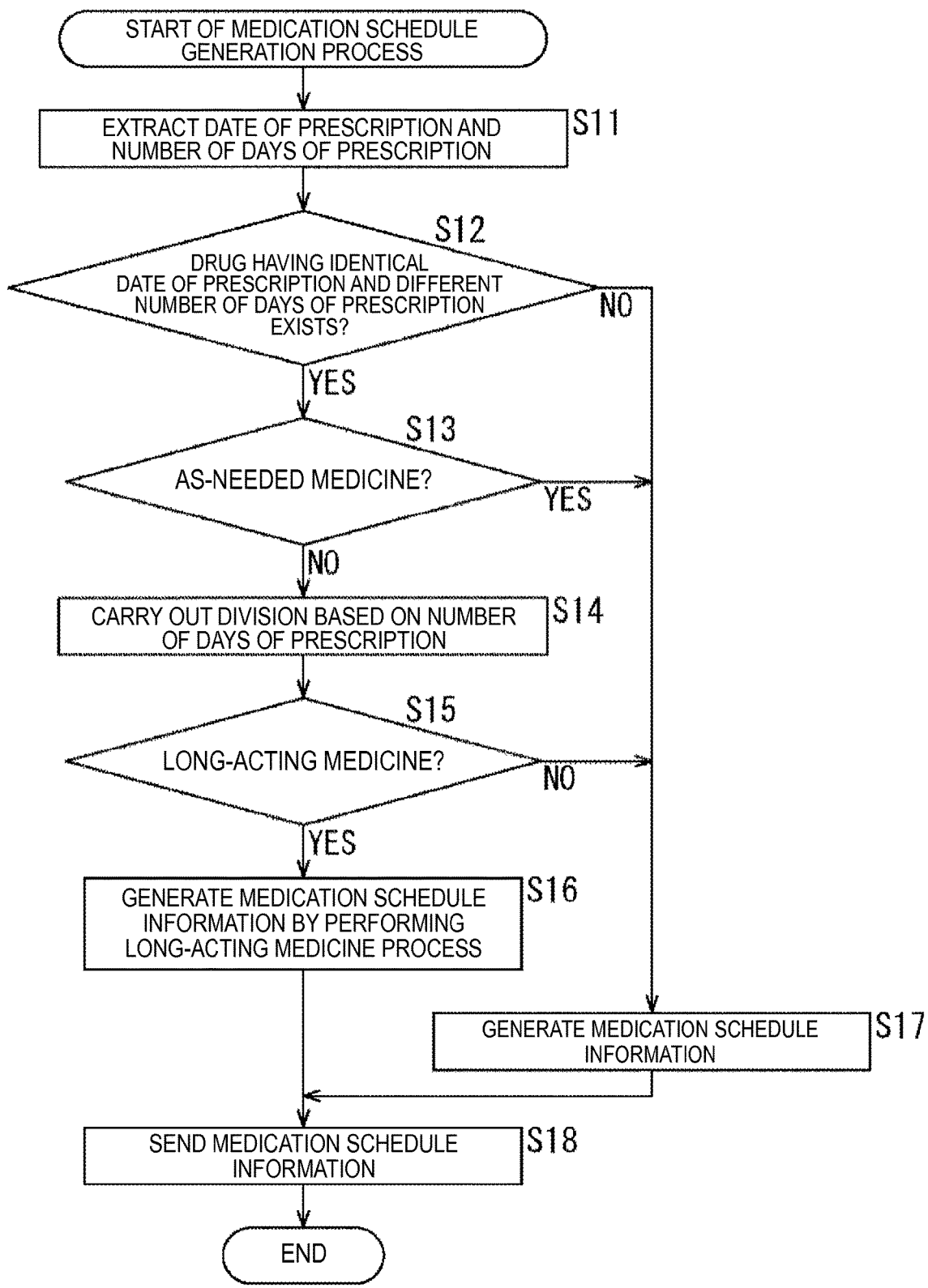
FIG. 3 is a flow chart illustrating medication schedule generation process.

Back to the description of the flow chart in FIG. 3, when generating the medication schedule information of each prescription drug, the medication schedule generation unit 54 supplies the medication schedule information thus obtained to the communication unit 41, and the process proceeds from step S16 to step S18.

In addition, when determined that there is no prescription drug having different numbers of days of prescription on an identical date of prescription, when determined as an as-needed medicine in step S13, or when determined not as a long-acting medicine in step S15, the process in step S17 is performed.

In step S17, the medication schedule generation unit 54 generates the medication schedule information for each prescription drug based on the date of prescription and the number of days of prescription of each prescription drug.

For example, it is assumed that medication schedule information is generated for the prescription drug A having a date of prescription Da and the number of days of prescription Ma and the prescription drug B having a date of prescription Db and the number of days of prescription Mb.

In this case, the medication schedule generation unit 54 generates medication schedule information indicating that the prescription drug A is taken in the period from the date of prescription Da to Da+Ma−1. Similarly, the medication schedule generation unit 54 generates medication schedule information indicating that the prescription drug B is taken in the period from the date of prescription Db to Db+Mb−1. When the medication schedule generation unit 54 supplies the medication schedule information thus obtained to the communication unit 41, the process proceeds to step S18.

When the process in step S17 is performed, since the prescription drugs subjected to the process are not long-acting medicines, the medication schedule of each prescription drug is considered to be a period of the number of days of prescription taking the date of prescription of the prescription drug as the starting date. It should be noted that, when the prescription drug is an as-needed medicine, medication schedule information of the as-needed medicine may be generated in a process specialized for as-needed medicines.

As the process in step S16 or step S17 is performed, the process in step S18 is performed after that.

That is to say, in step S18, the communication unit 41 sends the medication schedule information supplied from the medication schedule generation unit 54 to the portable terminal device 11, and the medication schedule generation process is finished. The medication schedule information sent to the portable terminal device 11 is utilized for various processes, such as detection of intake drug combination and detection of duplication, in the portable terminal device 11.

As described above, the data center 14 detects a long-acting medicine among the prescription drugs by comparing the date of prescription of each prescription drug and performing division based on the number of days of prescription of each prescription drug, and performs long-acting medicine process for the long-acting medicine to generate medication schedule information.

In such a manner, it is possible to obtain medication schedule information that indicates more probable medication schedule by detecting the long-acting medicine and generating medication schedule information for the long-acting medicine based on the number of days of prescription other prescription drugs prescribed on a same day. That is to say, it is possible to obtain more probable information on medication of prescription drugs.

By utilizing the medication schedule information thus obtained for an application program that detects a drug of contraindication or alert to intake combination, for example, it is possible to alert highly practically.

Specifically, when the medication schedule information illustrated in FIG. 5 is obtained, for example, it is possible to obtain probability of occurrence of intake combination of any two drugs by using the degrees of influence of prescription drugs at each date as a probability of medication of the prescription drugs by the patient. By taking the intake combination occurrence probability as a priority of intake combination of each prescription drug, it becomes possible to present a risk of combination of intake drugs to the user considering the priority.

For example, when a risk of combination of intake drugs is detected only for the drugs taken by a user on a specific date, it becomes not possible to detect a risk of potential intake combination that may occur due to medication delay or the like. That is, it becomes not possible to comprehensively detect risks of combination of intake drugs.

In addition, when risks of combination of intake drugs for all drugs that have been taken by a user currently or in the past are detected, the number of intake combination becomes enormous. Therefore, even though notes for alert on the risks of intake combination for all those combinations are presented to the user, there is a concern that such a note for alert is rather not read by the user.

In contrast, when the risk of combination of intake drugs is presented to the user considering the priority as described above, it is possible not only to detect more risks of intake combination but also possible to preferentially present higher possibilities to the user, and thus it is possible to give more effective medication instruction.

In addition, according to the present disclosure, it becomes possible to more confidently detect duplication of drugs, which has been a problem in recent years.

For example, it is assumed that a prescription drug C is prescribed for four times to a user and the effect of the prescription drug C due to the medication acts for seven days. In this case, the user is supposed to receive drugs for 28 days while the number of days of prescription of the prescription drug C that is extracted from the health insurance claims is for four days.

Therefore, assumed that a medication schedule (period of medication) of the prescription drug C is a period of the number of days of prescription taking the date of prescription as the starting date when the medication schedule information of the prescription drug C is generated, it is not possible to find duplication prescription even when the prescription drug C is prescribed in duplication after four days from the date of prescription of the prescription drug C.

However, in the present disclosure, when there is another prescription drug that is prescribed on a same day as the prescription drug C, the long-acting medicine process is performed for the prescription drug C and the medication schedule information is generated, so that there is a higher possibility to be able to find duplication prescription of the prescription drug C.

Second Embodiment

[Description of Medication Schedule Generation Process]

It should be noted that, although whether or not there is a possibility that a drug is a long-acting medicine is identified by determining whether or not there are prescription drugs having different numbers of days of prescription on an identical date of prescription in the medication schedule generation process in the above descriptions, such determination process may be not performed when there is available capacity in the calculation capability.

Figure 6:
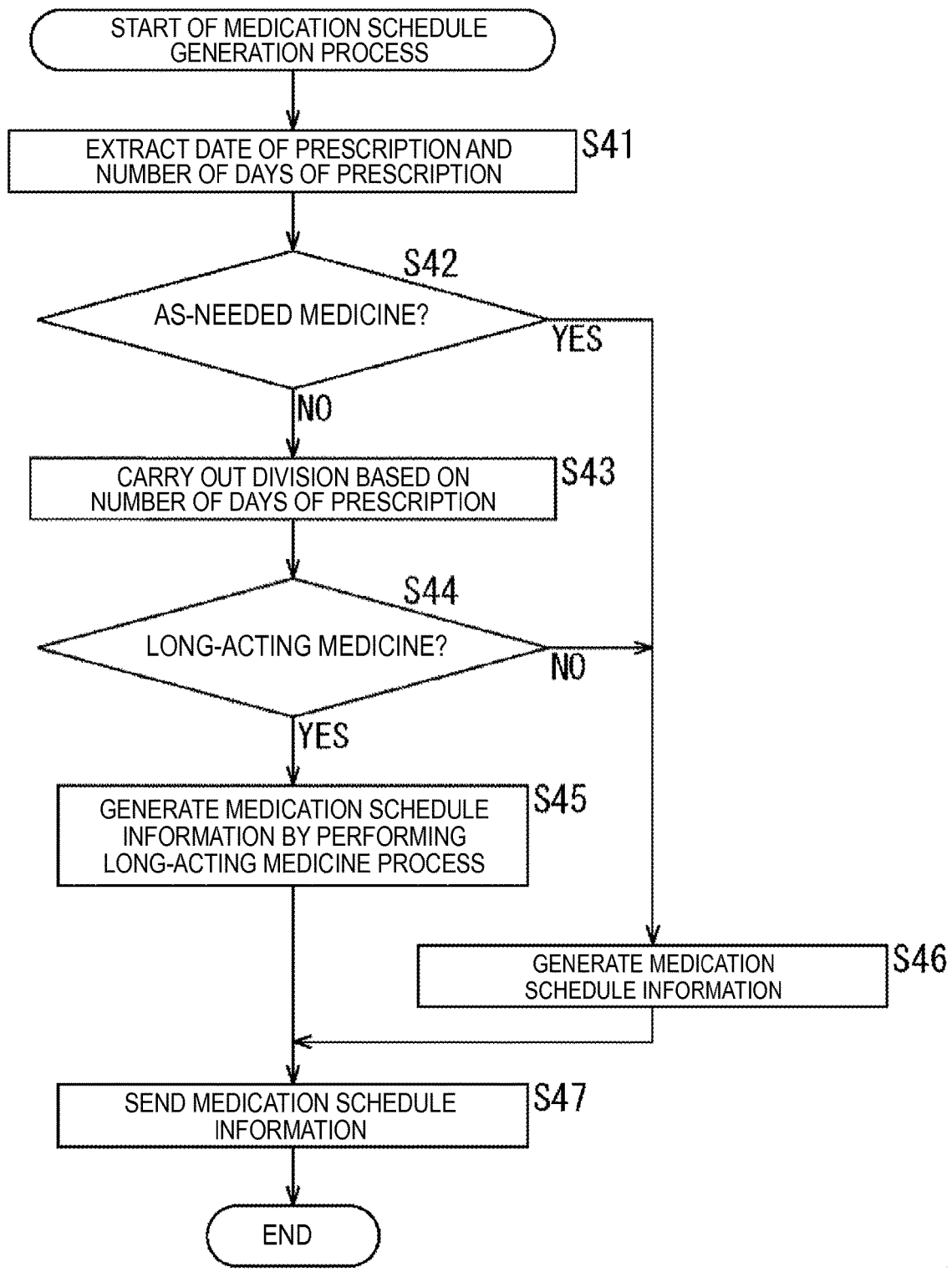
FIG. 6 is a flow chart illustrating medication schedule generation process.

In such a case, the data center 14 performs medication schedule generation process illustrated in FIG. 6. Descriptions are given below to medication schedule generation process by the data center 14 with reference to the flow chart in FIG. 6.

In step S41, the extraction unit 51 extracts a date of prescription and the number of days of prescription of each prescription drug as information on prescription drugs prescribed for a specific patient from the medication history information, such as the dispensation health insurance claim information, the medical health insurance claim information, and the DPC health insurance claim information recorded in the recording unit 44.

It should be noted that the respective prescription drugs are extracted from a same health insurance claim that is identified by a health insurance claim ID, so that the date of prescription of the prescription drugs is basically same.

As the date of prescription and the number of days of prescription of the prescription drugs are extracted, the processes in step S42 to step S47 are performed after that and the medication schedule generation process is finished while these processes are similar to the processes in step S13 to step S18 in FIG. 3, so that their descriptions are omitted.

For example, in the medication schedule generation process in FIG. 6, the process in step S12 in FIG. 3, that is, detection of prescription drugs having different numbers of days of prescription is not performed. However, even when medication schedule information is generated in the long-acting medicine process for the prescription drugs having a same number of days of prescription, for example, medication schedule information same as the case of not performing the long-acting medicine process is obtained as a result.

As described above, the data center 14 carries out division based on the number of days of prescription of each prescription drug, detects a long-acting medicine among the prescription drugs, and performs long-acting medicine process as needed to generate medication schedule information. It is thus possible to obtain medication schedule information that indicates a more probable medication schedule.

Third Embodiment

[Configuration Example of Portable Terminal Device]

Further, although an example in the case where the medication schedule information is generated by the data center 14 is described in the above descriptions, medication schedule information may also be generated by another device, such as the portable terminal device 11.

Figure 7:
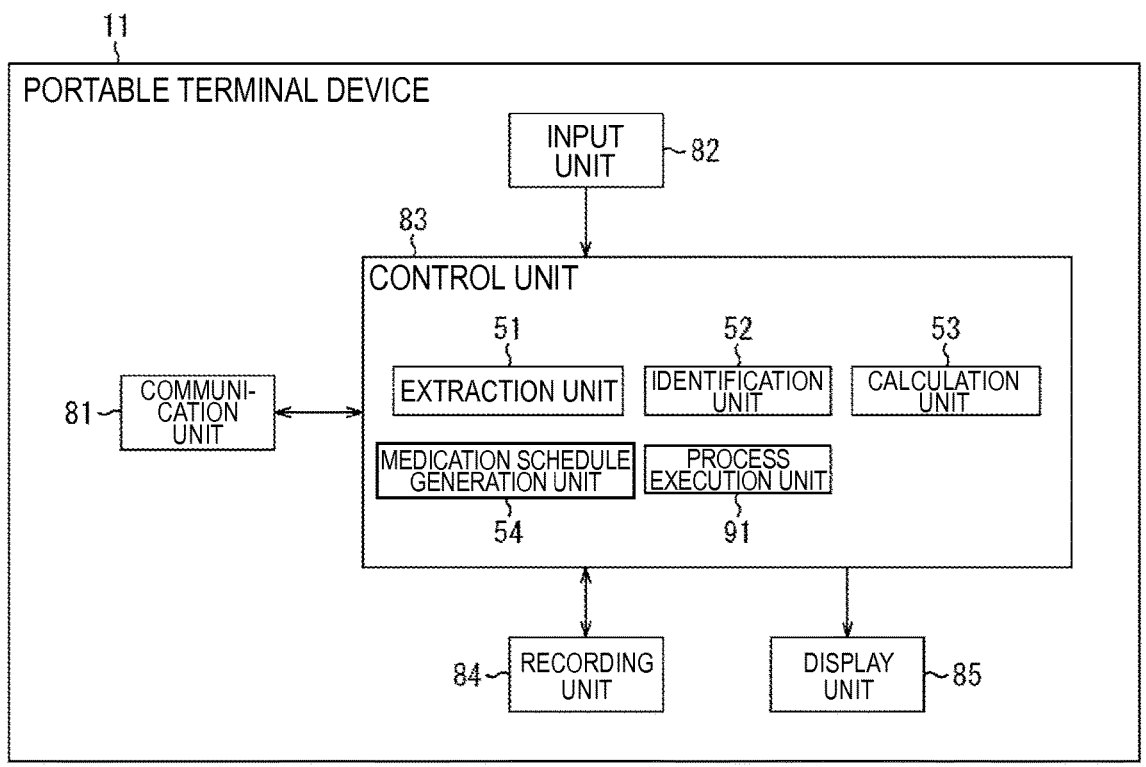
FIG. 7 is an illustration of a configuration example of a portable terminal device.

For example, when medication schedule information is generated by the portable terminal device 11, the portable terminal device 11 is configured as illustrated in FIG. 7. It should be noted that components in FIG. 7 corresponding to the case of FIG. 2 are denoted with the same reference signs, and the descriptions are omitted.

The portable terminal device 11 is configured with a communication unit 81, an input unit 82, a control unit 83, a recording unit 84, and a display unit 85.

The communication unit 81 communicates with an external device, such as the data center 14, to receive various types of data and supply the data to the control unit 83 and to send the data supplied from the control unit 83. The input unit 82 supplies information that is composed of, for example, input buttons, a touch screen, and the like and is inputted by a user to the control unit 83.

The control unit 83 controls a behavior of the entire portable terminal device 11. The control unit 83 is provided with the extraction unit 51, the identification unit 52, the calculation unit 53, the medication schedule generation unit 54, and a process execution unit 91.

The process execution unit 91 executes various processes, such as detecting a risk of combination of intake drugs and detecting duplication of drugs based on the medication schedule information generated by the medication schedule generation unit 54.

The recording unit 84 records programs that are executed by the control unit 83 and various types of data to supply the data to the control unit 83 as needed. For example, in the recording unit 84, medication history data that is acquired from the data center 14 or the like is recorded as Medication Notebook of a user.

The display unit 85 is composed of a liquid crystal display panel or the like and displays various images based on the data supplied from the control unit 83.

[Description of Medication Schedule Generation Process]

Figure 8:
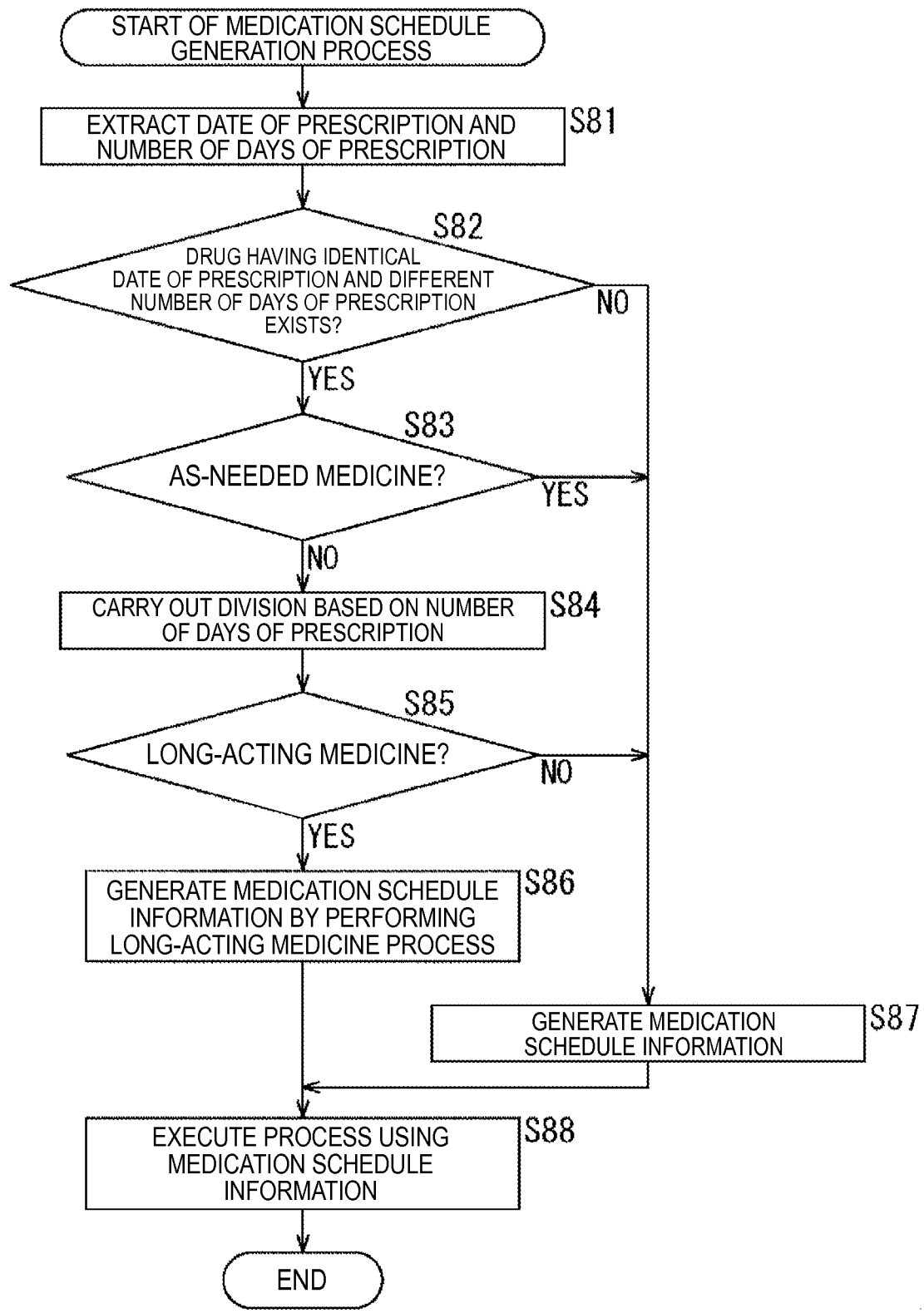
FIG. 8 is a flow chart illustrating medication schedule generation process.

Next, descriptions are given to medication schedule generation process performed by the portable terminal device 11 with reference to the flow chart in FIG. 8.

In step S81, the extraction unit 51 extracts a date of prescription and the number of days of prescription of each prescription drug, as the information on the prescription drugs that are prescribed, from the medication history data recorded in the recording unit 84. At this time, the extraction unit 51 extracts the dates of prescription and the numbers of days of prescription for the prescription drugs that are included in an identical health insurance claim.

It should be noted that the medication history information, such as the dispensation health insurance claim information, the medical health insurance claim information, and the DPC health insurance claim information, may be recorded in the recording unit 84 to extract the date of prescription and the number of days of prescription of each prescription drug from the medication history information. In addition, the extraction unit 51 may also acquire the date of prescription and the number of days of prescription by causing the communication unit 81 to receive the date of prescription and the number of days of prescription of each prescription drug included in the medication history information from the data center 14 or the like.

After the date of prescription and the number of days of prescription of each prescription drug are extracted, the processes in step S82 to step S87 are performed after that and medication schedule information of each prescription drug is generated. It should be noted that these processes are similar to the processes in step S12 to step S17 in FIG. 3, so that the descriptions are omitted.

As the medication schedule information is generated in step S86 or step S87, the process execution unit 91 executes predetermined process in step S88 using the medication schedule information. For example, the process execution unit 91 detects a risk of combination of intake drugs and detects duplication of drugs based on the medication schedule information. In addition, process of displaying the medication schedule information on the display unit 85 may also be performed.

As the process using the medication schedule information is executed by the process execution unit 91, the medication schedule generation process is finished after that.

In the manner described above, the portable terminal device 11 detects a long-acting medicine among prescription drugs by comparing the date of prescription of each prescription drug and carrying out division based on the number of days of prescription of each prescription drug, and performs long-acting medicine process for the long-acting medicine to generate medication schedule information.

As just described, it is possible to obtain medication schedule information that indicates a more probable medication schedule by detecting a long-acting medicine and generating medication schedule information for the long-acting medicine based on the number of days of prescription of other prescription drugs prescribed on a same day.

Fourth Embodiment

[Description of Medication Schedule Generation Process]

It should be noted that, although description has been given to the case of determining whether or not there are prescription drugs having different numbers of days of prescription on an identical date of prescription in the medication schedule generation process that is performed by the portable terminal device 11 in the above descriptions, such determination process may be not performed.

Figure 9:
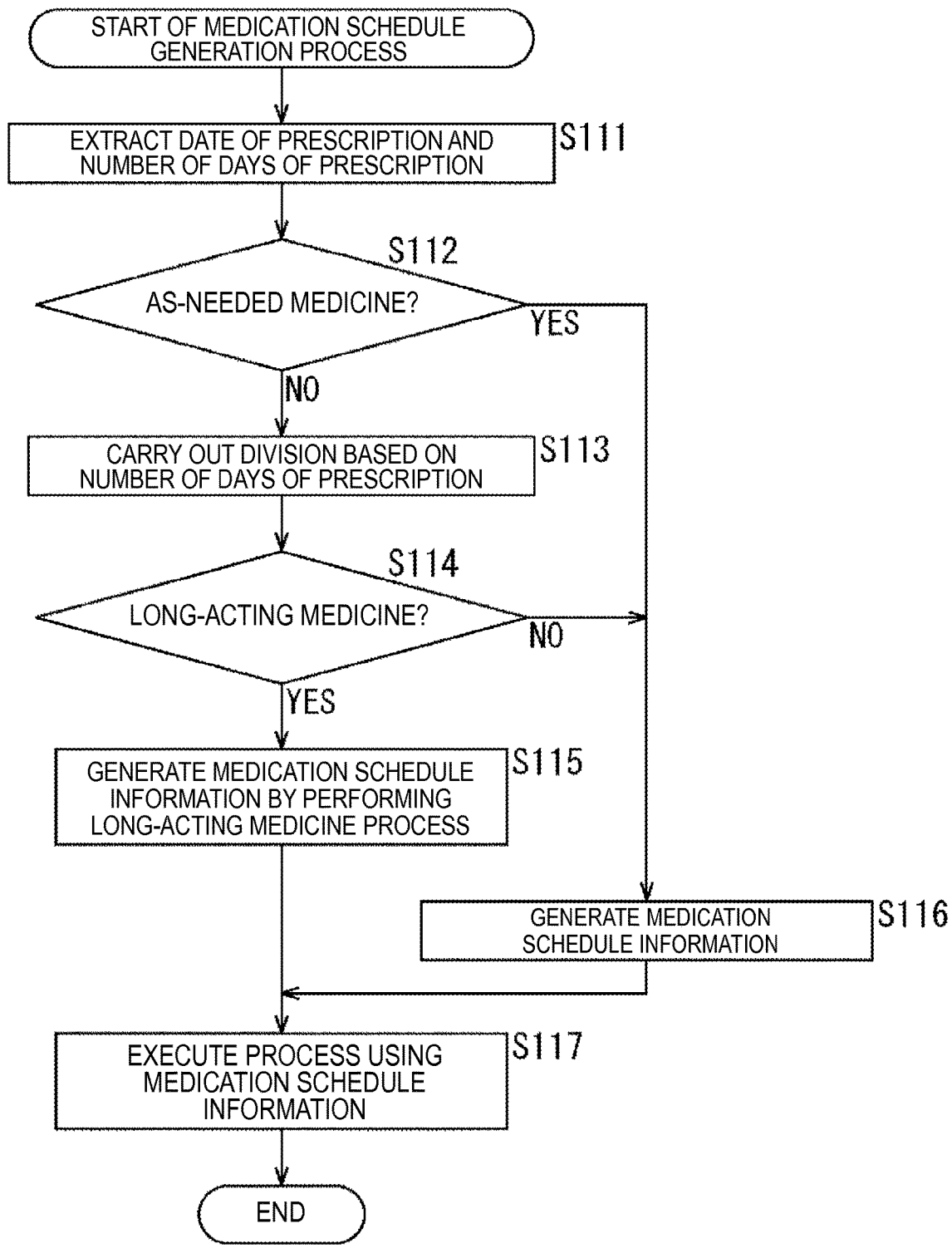
FIG. 9 is a flow chart illustrating medication schedule generation process.

In such a case, the portable terminal device 11 performs medication schedule generation process illustrated in FIG. 9. Descriptions are given below to medication schedule generation process by the portable terminal device 11 with reference to the flow chart in FIG. 9.

In step S111, the extraction unit 51 extracts a date of prescription and the number of days of prescription of each prescription drug, as information on the prescription drugs that are prescribed, from the medication history data recorded in the recording unit 84 for the prescription drugs that are included in an identical health insurance claim.

As the date of prescription and the number of days of prescription of the prescription drugs are extracted, the processes in step S112 to step S117 are performed after that and the medication schedule generation process is finished, and these processes are similar to the processes in step S83 to step S88 in FIG. 8, so that the descriptions are omitted.

In the manner described above, the portable terminal device 11 carries out division based on the number of days of prescription of each prescription drug, detects a long-acting medicine among the prescription drugs, and performs the long-acting medicine process as needed to generate medication schedule information. It is thus possible to obtain medication schedule information that indicates a more probable medication schedule.

The series of processes described above can be executed by hardware but can also be executed by software. When the series of processes is executed by software, a program that constructs such software is installed into a computer. Here, the expression "computer" includes a computer in which dedicated hardware is incorporated and a general-purpose personal computer or the like that is capable of executing various functions when various programs are installed.

FIG. 10 is a block diagram showing a hardware configuration example of a computer that performs the above-described series of processing using a program.

In the computer, a central processing unit (CPU) 201, a read only memory (ROM) 202 and a random access memory (RAM) 203 are mutually connected by a bus 204.

An input/output interface 205 is also connected to the bus 204. An input unit 206, an output unit 207, a recording unit 208, a communication unit 209, and a drive 210 are connected to the input/output interface 205.

The input unit 206 is configured from a keyboard, a mouse, a microphone, an image sensor, or the like. The output unit 207 is configured from a display, a speaker or the like. The recording unit 208 is configured from a hard disk, a non-volatile memory or the like. The communication unit 209 is configured from a network interface or the like. The drive 210 drives a removable medium 211 such as a magnetic disk, an optical disk, a magneto-optical disk, a semiconductor memory or the like.

In the computer configured as described above, the CPU 201 loads a program that is recorded, for example, in the recording unit 208 onto the RAM 203 via the input/output interface 205 and the bus 204, and executes the program. Thus, the above-described series of processing is performed.

Programs to be executed by the computer (the CPU 201) are provided being recorded in the removable medium 211 which is a packaged medium or the like. Also, programs may be provided via a wired or wireless transmission medium, such as a local area network, the Internet or digital satellite broadcasting.

In the computer, by loading the removable recording medium 211 into the drive 210, the program can be installed into the recording unit 208 via the input/output interface 205. It is also possible to receive the program from a wired or wireless transfer medium using the communication unit 209 and install the program into the recording unit 208. As another alternative, the program can be installed in advance into the ROM 202 or the recording unit 208.

It should be noted that the program executed by a computer may be a program that is processed in time series according to the sequence described in this specification or a program that is processed in parallel or at necessary timing such as upon calling.

An embodiment of the disclosure is not limited to the embodiments described above, and various changes and modifications may be made without departing from the scope of the disclosure.

For example, the present disclosure can adopt a configuration of cloud computing which processes by allocating and connecting one function by a plurality of devices through a network.

Further, each step described by the above mentioned flow charts can be executed by one device or by allocating a plurality of devices.

In addition, in the case where a plurality of processes is included in one step, the plurality of processes included in this one step can be executed by one device or by allocating a plurality of devices.

Additionally, the present technology may also be configured as below.

(1)

An information processing device including:

an acquisition unit configured to acquire a date of prescription of a prescription drug and the number of days of prescription of the prescription drug;

a calculation unit configured to carry out division based on the number of days of prescription of the prescription drug and the number of days of prescription of another prescription drug and identify whether or not the prescription drug is a long-acting medicine based on whether or not a result of the division satisfies a predetermined condition; and a medication schedule generation unit configured to generate medication schedule information of the prescription drug based on the date of prescription of the prescription drug and the number of days of prescription of the other prescription drug when the prescription drug is the long-acting medicine.

(2)

The information processing device according to (1), wherein the calculation unit carries out division based on the number of days of prescription of the prescription drug and the number of days of prescription of the other prescription drug having a date of prescription same as the prescription drug.

(3)

The information processing device according to (1) or (2), wherein the medication schedule generation unit generates the medication schedule information on an assumption that the number of days of prescription of the prescription drug is same as the number of days of prescription of the other prescription drug.

(4)

The information processing device according to (3), wherein the medication schedule generation unit divides a period of the number of days of prescription of the other prescription drug having the date of prescription of the prescription drug as a starting date into the number of divided periods same as the number of days of prescription of the prescription drug that is acquired by the acquisition unit, and generates the medication schedule information that indicates a medication schedule and a degree of influence of the prescription drug in a manner that the degree of influence due to the prescription drug attenuates from a starting date to a finishing date of the divided period in each of the divided periods.

(5)

The information processing device according to any one of (1) to (4), wherein the calculation unit assumes that the prescription drug is the long-acting medicine when a reminder of Ma/Mb is 0 in a case where the number of days of prescription of the other prescription drug is Ma, the number of days of prescription of the prescription drug is Mb, and Ma>Mb.

(6)

The information processing device according to any one of (1) to (4), wherein the calculation unit assumes that the prescription drug is the long-acting medicine when a quotient of Ma/(Mb−1) is any one of 7, 14, or 28 to 31 in a case where the number of days of prescription of the other prescription drug is Ma, the number of days of prescription of the prescription drug is Mb, and Ma>Mb.

(7)

The information processing device according to any one of (1) to (6), further including an identification unit configured to identify whether or not there is the other prescription drug having a date of prescription identical to the prescription drug and also having the number of days of prescription different from the prescription drug.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST 11 portable terminal device
14 data center
41 communication unit
44 recording unit
51 extraction unit
52 identification unit
53 calculation unit
54 medication schedule generation unit
91 process execution unit

The invention claimed is:

1. An information processing device, comprising:
a central processing unit (CPU) configured to:
   extract, from medical history information, a date of a prescription of each of at least two prescription drugs and a number of days of the prescription for each of the at least two prescription drugs;
   determine that a first date of the prescription of a first prescription drug of the at least two prescription drugs is same as a second date of the prescription of a second prescription drug of the at least two prescription drugs, based on the extraction,
   wherein a number of days of the prescription of the first prescription drug is different from a number of days of the prescription of the second prescription drug;
   divide the number of days of the prescription of the first prescription drug by the number of days of the prescription of the second prescription drug;
   determine that the second prescription drug is a long-acting medicine based on a result of the division that satisfies a specific condition;
   divide, based on the determination that the second prescription drug is the long-acting medicine, the number of days of the prescription of the second prescription drug into a number of divided periods such that a number of days of the divided periods is same as the number of days of the prescription of the first prescription drug,
   wherein the first date is a starting date of user intake of the first prescription drug, and the second date is a starting date of user intake of the second prescription drug;
   generate medication schedule information of the at least two prescription drugs that indicates a medication schedule and a degree of influence of the second prescription drug such that the degree of influence of the second prescription drug attenuates from the starting date of user intake of the second prescription drug to a finishing date in each of the divided periods,
   wherein the generation of the medication schedule information is based on the starting date of user intake of the second prescription drug, and the number of days of the prescription of the first prescription drug; and
   transmit the medication schedule information to a portable terminal device.

2. The information processing device according to claim 1,
wherein the CPU is further configured to divide the number of days of the prescription of the second prescription drug into the number of divided periods, based on the number of days of the prescription of the first prescription drug and the number of days of the prescription of the second prescription drug.

3. The information processing device according to claim 2, wherein the CPU is further configured to generate the medication schedule information based on an assumption that the number of days of the prescription of the first prescription drug is same as the number of days of the prescription of the second prescription drug.

4. The information processing device according to claim 2, wherein the CPU is further configured to determine that the second prescription drug is the long-acting medicine based on a reminder of Ma/Mb is 0, and wherein
the number of days of the prescription of the first prescription drug is Ma,
the number of days of the prescription of the second prescription drug is Mb, and Ma is greater than Mb.

5. The information processing device according to claim 2,
wherein the CPU is further configured to determine that the second prescription drug is the long-acting medicine based on a quotient of a division of Ma by Mb−1, wherein the quotient is one of 7, 14, or 28 to 31, and wherein
the number of days of the prescription of the first prescription drug is Ma,
the number of days of the prescription of the second prescription drug is Mb, and
Ma is greater than Mb.

6. An information processing method, comprising:
extracting, from medical history information, a date of a prescription of each of at least two prescription drugs and a number of days of the prescription for each of the at least two prescription drugs;
determining that a first date of the prescription of a first prescription drug of the at least two prescription drugs is same as a second date of the prescription of a second prescription drug of the at least two prescription drugs, based on the extraction,
wherein a number of days of the prescription of the first prescription drug is different from a number of days of the prescription of the second prescription drug;
dividing the number of days of the prescription of the first prescription drug by the number of days of the prescription of the second prescription drug;
determining that the second prescription drug is a long-acting medicine based on a result of the division that satisfies a specific condition;
dividing, based on the determination that the second prescription drug is the long-acting medicine, the number of days of the prescription of the second prescription drug into a number of divided periods such that a number of days of the divided periods is same as the number of days of the prescription of the first prescription drug,
wherein the first date is a starting date of user intake of the first prescription drug, and the second date is a starting date of user intake of the second prescription drug;
generating medication schedule information of the at least two prescription drugs that indicates a medication schedule and a degree of influence of the second prescription drug such that the degree of influence of the second prescription drug attenuates from the starting date of user intake of the second prescription drug to a finishing date in each of the divided periods,
wherein the generation of the medication schedule information is based on the starting date of user intake of the second prescription drug, and the number of days of the prescription of the first prescription drug; and
transmitting the medication schedule information to a portable terminal device.

7. A non-transitory computer-readable storage medium having stored thereon computer-executable instructions for causing a computer to execute operations, the operations comprising:
extracting, from medical history information, a date of a prescription of each of at least two prescription drugs and a number of days of the prescription for each of the at least two prescription drugs;
determining that a first date of the prescription of a first prescription drug of the at least two prescription drugs is same as a second date of the prescription of a second prescription drug of the at least two prescription drugs, based on the extraction,
wherein a number of days of the prescription of the first prescription drug is different from a number of days of the prescription of the second prescription drug;
dividing the number of days of the prescription of the first prescription drug by the number of days of the prescription of the second prescription drug;
determining that the second prescription drug is a long-acting medicine based on a result of the division that satisfies a specific condition;
dividing, based on the determination that the second prescription drug is the long-acting medicine, the number of days of the prescription of the second prescription drug into a number of divided periods such that a number of days of the divided periods is same as the number of days of the prescription of the first prescription drug,
wherein the first date is a starting date of user intake of the first prescription drug, and the second date is a starting date of user intake of the second prescription drug;
generating medication schedule information of the at least two prescription drugs that indicates a medication schedule and a degree of influence of the second prescription drug such that the degree of influence of the second prescription drug attenuates from the starting date of user intake of the second prescription drug to a finishing date in each of the divided periods,
wherein the generation of the medication schedule information is based on the starting date of user intake of the second prescription drug and the number of days of the prescription of the first prescription drug; and
transmitting the medication schedule information to a portable terminal device.

* * * * *